United States Patent [19]

Smith

[11] Patent Number: 4,637,512
[45] Date of Patent: Jan. 20, 1987

[54] TOOTHPICK DISPENSER

[76] Inventor: Forrest D. Smith, P.O. Box 3784, Eureka, Calif. 95501

[21] Appl. No.: 771,065

[22] Filed: Aug. 30, 1985

[51] Int. Cl.⁴ ............................................. B65D 85/28
[52] U.S. Cl. .................................. 206/103; 206/383; 206/382; 206/380
[58] Field of Search ............... 206/382, 383, 380, 346, 206/347, 102, 103

[56] References Cited

U.S. PATENT DOCUMENTS

| | | | |
|---|---|---|---|
| 40,305 | 10/1863 | Blood et al. | 206/382 |
| 121,860 | 12/1871 | Evans | 206/382 |
| 1,106,773 | 8/1914 | Brabant | 206/382 |
| 1,634,096 | 6/1927 | Doscher | 206/382 |
| 1,856,559 | 5/1932 | Johnson | 206/380 |
| 2,111,265 | 3/1938 | Heckel | 206/382 |
| 2,394,457 | 2/1946 | Lobl | 206/380 |
| 2,678,673 | 5/1954 | Sheils | 206/38 |
| 4,386,697 | 6/1983 | Zocher | 206/383 |

FOREIGN PATENT DOCUMENTS 99 of 1853 United Kingdom ................ 206/380

Primary Examiner—Joseph Man-Fu Moy
Attorney, Agent, or Firm—Bruce A. Jagger; Natan Epstein

[57] ABSTRACT

A combination toothpick dispenser/matchbook is disclosed in comprising a matchbook provided with a cover foldable against an opposite match-carrying portion of the matchbook, the cover having an inside surface, a toothpick dispenser attached to the inside surface, the dispenser including a pocket for receiving lower ends of toothpicks inserted therein, a retainer for holding the intermediate portions of the toothpicks flat against the inner cover surface, and a flap covering the upper ends of the toothpicks, both ends of the toothpick, that being cover for sanitary purposes and security while being readily accessible for individual removal. The combined matchbook/toothpick dispenser is disclosed in two different embodiments and a separate self-contained toothpick dispenser is also disclosed.

20 Claims, 7 Drawing Figures

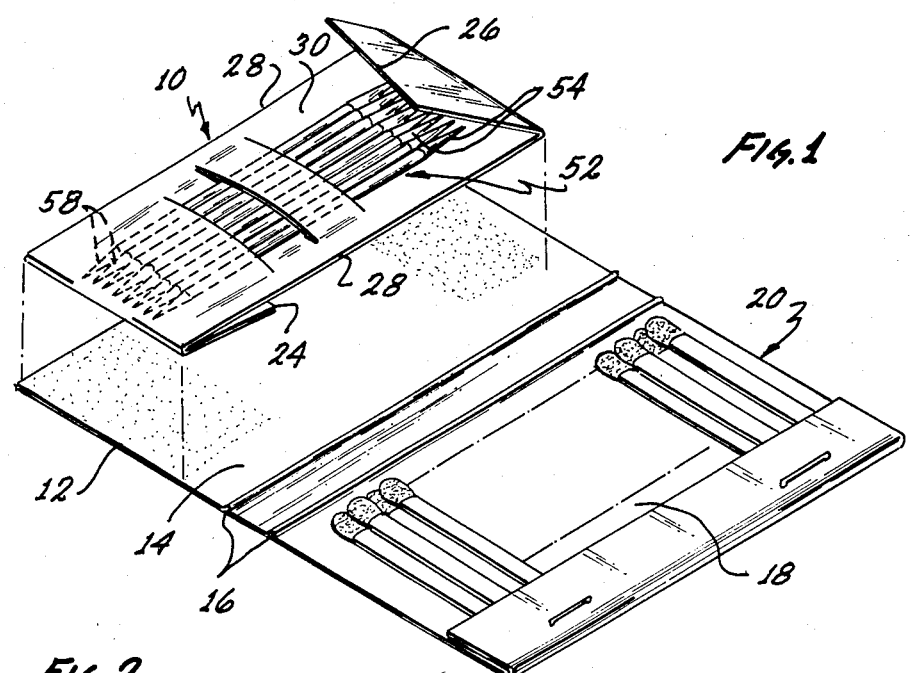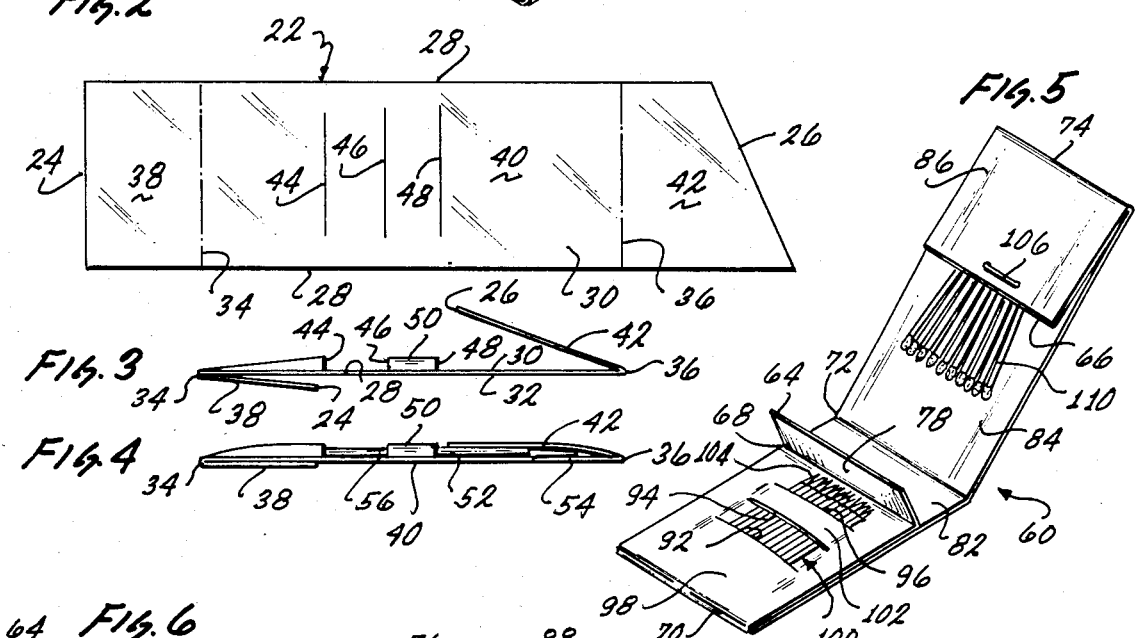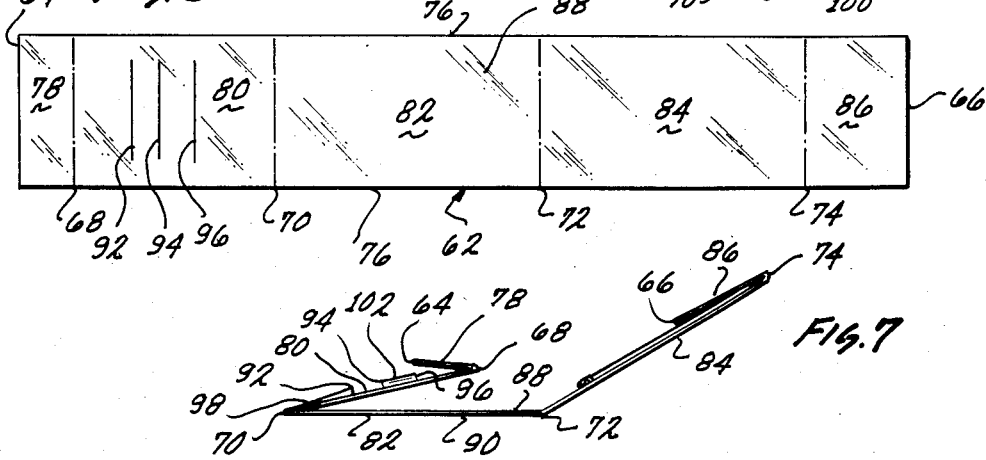

4,637,512

TOOTHPICK DISPENSER

BACKGROUND OF THE INVENTION

1. Field of the Invention

The present invention pertains generally to the field of toothpick dispensers and is more particularly directed to toothpick dispensers useful in combination with a matchbook or as a self-contained unit for conveniently carrying a supply of toothpicks in a wallet or in a pocket.

2. State of the Prior Art

Applicant is not aware of similar existing toothpick carriers or dispensers.

SUMMARY OF THE INVENTION

The present invention includes both a toothpick carrier/dispenser which is useful either as a self contained unit and as such may be carried in a pocket or wallet so as to keep a supply of toothpicks available at all times, or in combination with a matchbook so as to make available a supply of both toothpicks and matches in one convenient, easily carried and inexpensive unit.

Two different versions of the combination toothpick dispenser/matchbook unit are disclosed. A first such combination is based on a conventional matchbook to which is affixed on an inside cover surface a toothpick dispenser disclosed herein. In the second such combination, a novel toothpick dispenser/matchbook unit is disclosed. In any of the above mentioned forms of the present invention, the novel toothpick dispensers are particularly useful as low cost and unique promotional items on which may be printed or otherwise displayed advertising matter.

In general, the combination matchbook/toothpick dispenser of this invention may be characterized as comprising a matchbook provided with a cover foldable against an opposite match-carrying portion of the matchbook, the cover having an inside surface, first means defining a pocket for receiving the lower ends of toothpicks inserted therein, a retainer for holding the intermediate portions of the toothpicks flat against the inner cover surface, and second means for covering the upper ends of the toothpicks, both ends of the toothpicks thus being covered for sanitary purposes, the retainer serving to hold the toothpicks within the container securely to prevent them from falling out at any time.

In a first embodiment of the invention, the toothpick dispenser comprises an elongated sheet of thin pliable material having a top side, an underside, two side edges and two ends. The sheet is divided by first and second fold lines into an upper flap, a lower flap and a main panel intermediate the two flaps. First, second and third cuts are made in the main panel transversely to the sheet and terminating short of the side edges. The lower flap is folded against the underside of the main panel so as to define a pocket for receiving the lower ends of toothpicks inserted through the first cut in the panel. The second and third cuts define a retainer band for holding the intermediate portion of toothpicks inserted under the band flat against the top side of the main panel. The upper flap is foldable over the upper end of the toothpicks held in the dispenser and against the top side of the main panel. A number of toothpicks can be packaged into the dispenser in mutually parallel, side by side relationship, on and against the top side of the main panel, except for the lower ends of the toothpicks which past through the first cut in the main panel to the underside of the dispenser and into the fold defined between the main panel and the lower flap folded thereunder. Both ends of the toothpicks are kept in clean sanitary condition by the flaps folded over the toothpick ends, yet the toothpicks remain readily accessible by lifting one of the flaps. Each toothpick can be easily removed from the dispenser without disturbing the remaining supply.

In a second embodiment of the invention, a combination matchbook/toothpick dispenser comprises an elongated sheet having two sides and two ends and which is divided by three fold lines tranverse to the sides into an upper flap, a main panel, and first and second book cover portions. Three cuts are made in the main panel. The combination matchbook/toothpick unit is formed by folding the top of the main panel against the top of the first cover portion, and the lower flap against the underside of the main panel. Finally, the two cover portion are folded with their topsides against each other. The three cuts in the main panel define a slit through which the toothpicks are inserted into the fold between the main panel and the first book cover portion, the other two cuts defining a retainer band for retaining the intermediate portion of toothpicks against the underside of the main panel. Finally the lower flap is folded down over the upper ends of toothpicks to provide sanitary protection and to prevent the toothpicks from escaping from the holder. A set of matches may be attached to the second book cover which will thus be opposite the toothpick dispenser on the first cover. The book is foldable along the third fold line between an open and a closed position and in the open position presents a toothpick dispenser on one cover and a matchbook on the other cover.

In either embodiment disclosed herein, the toothpick dispenser can be made inexpensively in great numbers from very low cost material. Either version can be made from a single strip of paper.

These and other advantages will be better understood by reference to the following drawings taken in light of the detailed description of the preferred embodiments.

BRIEF DESCRIPTION OF THE DRAWINGS

FIG. 1 illustrates in exploded relationship a conventional matchbook to which is attached a toothpick carrier/dispenser according to this invention.

FIG. 2 is a plan view of a sheet with the three cuts and two fold lines prior to folding into the unit of FIG. 1.

FIG. 3 is a side view of the sheet of FIG. 2 with partially folded end flaps.

FIG. 4 is a side view of the fully loaded toothpick dispenser made by folding the sheet of FIG. 3.

FIG. 5 is a perspective view of an alternate combination matchbook/toothpick dispenser according to the present invention.

FIG. 6 is a plan view of an elongated strip of paper with the cuts and fold lines prior to folding into the unit of FIG. 5.

FIG. 7 shows the strip of FIG. 6 partially folded to make the unit of FIG. 5.

DETAILED DESCRIPTION OF THE PREFERRED EMBODIMENTS

With reference to the drawings and FIG. 1 in particular, a toothpick dispenser unit 10 affixed to a conventional matchbook 20. The matchbook includes a cover 12 having an inside surface 14 which is foldable along bend lines 16 against an opposite match carrying portion 18.

The toothpick dispenser 10 is formed by folding a single, elongated sheet of paper 22 shown in FIG. 2. The sheet 22 has a lower end 24, an upper end 26 two parallel sides 28 extending between the two ends, a top side 30 and an underside 32 not visible in FIG. 2 but opposite to the top side 30 as a shown in FIGS. 3 and 4. The sheet 22 is creased or scored to make a first bend line 34 and a second bend line 36, which are parallel to each other and perpendicular to the sides 28. The two fold lines 34, 26 divide the sheets 22 into a lower flap 38, a main panel 40 and an upper flap 42. First, second and third cuts 44, 46 and 48 are made in the main panel 40 parallel to each other and to the bend lines. The three cuts terminate short of the sides 28 as shown.

The lower flap 38 is folded along the bend line 34 against the underside 32 of the sheet 22 as shown sequentially in FIGS. 3 and 4. One or more toothpicks may then be inserted into the novel dispenser by first passing the lower end of each toothpick under the paper retainer band 50 defined between the parallel cuts 46 and 48, and then through the cut 44 into the fold or pocket defined between the lower flap 38 and the underside of the main panel 24, as illustrated in FIGS. 1 and 4. The top flap 42 can then be folded along the second fold line 36 down against the top side of the main panel 40 and thus over and covering the upper ends 54 of toothpicks 52. The intermediate portions 56 of the toothpicks 52 are held flat against the top side 30 of the main panel as best appreciated in FIG. 4, and the lower ends 58 are held between the lower flap 24 and the underside of the main panel 40.

It will be appreciated that both ends of the toothpicks are covered for sanitary purposes and as a means of guaranteeing their staying in place, while allowing easy access for removal of individual toothpicks by lifting up the upper flap 26 and pulling out the selected toothpick. It is preferable that a single layer of toothpicks be carried in the dispenser 10, the combined width of the toothpicks extending the length of the retainer band 50 such that the toothpicks are packed in close side by side parallel relationship within the dispenser in a sanitary, esthetically pleasing package.

The dispenser/carrier 10 FIG. 1 may be used as a self-contained unit or in conjunction with matchbook 20 illustrated in FIG. 1. An alternative form of the present invention is illustrated in FIG. 5 which combines the toothpick dispenser and matchbook in an integrated unit 60 which is made from a single strip of paper 62 shown in FIG. 6. The strip of paper has a lower end 64, an upper end 66 and is creased or scored to form four spaced apart, mutually parallel bend or fold lines 68, 70, 72 and 74 which are perpendicular to the parallel sides 76 of the strip of paper. The four score lines define a lower flap 78, a main panel 80, a first cover portion 82, a second cover portion 84, and an upper flap 86. The sheet of paper 62 of FIG. 6 is folded as shown in the side view of FIG. 7 into the final product of FIG. 5. For purposes of explanation, the strip of paper 62 may be said to have a top side 88 and an underside 90 seen in FIG. 7. The main panel 80 is folded with its top side against the top side of the first cover portion 82, while the lower flap 78 is folded with its underside against the underside of the main panel 80. The top side of the upper flap 86 is folded along bend line 74 against the top side of the second cover portion 84. Finally the two cover portions are folded together in opposing relationship along bend line 72. The toothpick dispenser portion of this alternate form of the invention is similar to the structure of the dispenser of FIGS. 1 through 4. Three parallel cuts 92, 94 and 96 are made in the main panel 80, parallel to the crease line 68 through 74 and perpendicular to the side edges 76. Each of the cuts 92 through 96 terminates short of the side edges 76. The purpose of these three cuts is similar to that of the cuts 44, 46 and 48 in FIGS. 2 through 4. Thus a pocket 98 is formed between the top side of the panel 80 and the top side of the first cover portion 82. The lower ends of toothpicks 100 may be inserted through the cuts 92 into the pocket 98 as shown in FIG. 5. The middle or intermediate portion of each toothpick 100 is held flat against the underside of the main panel 80 by a retainer band 102 defined between the cuts 94 and 96. The upper ends 104 of the toothpicks are covered for sanitary purposes and for security by the lower flap 78.

A plurality of paper matches may be attached to the second cover portion 84 as by stapling at 106 between the upper flap 86 and the second portion 84. It will be understood that the upper flap 86 may be omitted, if desired, and the matches 110 secured to the second cover portion 84 by suitable alternate means.

The toothpick dispenser 10 of FIG. 1 may be affixed to the inside surface 14 of the matchbook cover 12 as by gluing both the under side of the main panel 40 and the top side of the lower flap 38 the inside surface 14. The top flap 26 remains free for lifting so as to allow access to the toothpicks 52.

It will be appreciated that either form of the invention disclosed herein can be arrived at by alternate constructions requiring more than a single piece of paper or similar structural material. Thus the various panels may be separate pieces of material secured together in suitable manner to arrive at the toothpick dispenser structures disclosed herein. Therefore, although particular embodiments of the invention have been described and illustrated for purposes of clarity, still other modifications, changes and substitutions will become apparent to those possessed of ordinary skill in the art. The scope of the invention is therefore not to be limited by the foregoing description but only by the following claims.

What is claimed is:

1. A toothpick dispenser useful for attachment to a matchbook cover comprising:
   an elongated sheet of thin pliable material having a top side, an underside, two side edges and two ends;
   first and second fold lines dividing said sheet into an upper flap, a lower flap and a main panel intermediate said flaps;
   first, second and third cuts in said main panel terminating short of said side edges;
   said lower flap being folded against the underside of said main panel to define a pocket for receiving the lower ends of toothpicks inserted through said first cut;
   said second and third cuts defining a retainer band for holding an intermediate portion of toothpicks inserted thereunder flat against the top side of said main panel;
   said upper flap being foldable over the upper ends of the toothpicks and against the topside of the main panel.

2. The toothpick dispenser of claim 1 further comprising a matchbook including a matchbook cover, said underside being affixed to said matchbook cover.

3. The dispenser of claim 2 wherein said matchbook cover has an inner side foldable against an opposite matchbook portion, said underside being affixed to said inner side such that the toothpick dispenser is enclosed within said matchbook when the matchbook is closed, the matchbook cover thus keeping said upper flap folded over the upper ends of the toothpicks.

4. The dispenser of claim 2 wherein said underside is affixed by gluing to said matchbook cover.

5. The dispenser of claim 1 wherein said sheet is a sheet of paper.

6. The dispenser of claim 1 wherein said sides are mutually parallel.

7. The dispenser of claim 1 wherein said first, second and third cuts are mutually parallel.

8. The dispenser of claim 1 wherein said sides are mutually parallel and said first, second and third cuts are mutually parallel and perpendicular to said sides.

9. A combination matchbook/toothpick dispenser comprising an elongated sheet having two sides and two ends, first, second and third fold lines transverse to said sides, first, second and third cuts intermediate said first and second fold lines and terminating short of said sides, said fold lines defining an upper flap between one end and said first fold line, a main panel between said first and second fold line, a first book cover between said second and third fold lines, and a second book cover between said third fold line and the other of said ends, said first and second cuts defining a retainer band for holding toothpicks thereunder with the upper ends of said toothpicks flat against one side of said main panel and under said upper flap, the lower ends of said toothpicks passing through said third cut and lying between the opposite side of said main panel and said first match cover.

10. The combination of claim 9 further comprising a plurality of matches attached to said second book cover.

11. The combination of claim 9 further comprising a fourth fold line defining an end flap with said other end folded against said second cover, there being a plurality of matches secured between said end flap and said second cover.

12. The combination of claim 9 wherein said strip has a top side and an underside, the topside of said main panel being folded against the top side of said first cover, said third cut allowing insertion of the lower ends of toothpicks between said main panel and said first cover, said first and second cuts defining a retaining band for holding intermediate parts of toothpicks inserted thereunder flat against the underside of said main panel, said lower flap being foldable over the upper ends of the toothpicks such that both ends of the toothpicks are kept in sanitary condition while in said dispenser.

13. The combination of claim 12 further comprising a fourth fold line defining an end flap with said other end, said end flap being folded against said second cover, there being a plurality of matches secured between said end flap and said second cover thereby forming a book foldable along said third fold line between an open and a closed position, said book in the open position presenting a toothpick dispenser on one cover and matches on the other cover.

14. The combination of claim 12 wherein said main panel is affixed to said first cover in said folded condition.

15. The combination of claim 13 wherein said matches are secured between said end flap and said second cover by stapling.

16. The combination of claim 12 wherein said sides are mutually parallel and said cuts are mutually parallel but perpendicular to said sides.

17. A toothpick dispenser useful for attachment to a matchbook comprising an elongated sheet of pliable material, two transverse fold lines in said sheet defining a panel between two end flaps, each said flap being folded against an opposite side of said panel, first and second cuts in said panel defining a retainer band for holding an intermediate portion of toothpicks inserted thereunder flat against a top side of said panel, a third cut in said panel for admitting the lower ends of said toothpicks through said panel and under one said flap folded against the underside of said panel, the other said flap covering the upper ends of the toothpicks on the top side of said panel.

18. The toothpick dispenser of claim 17 wherein said underside of the panel is affixed to a matchbook.

19. The toothpick dispenser of claim 17 wherein said flap folded against said underside is relatively long and is folded to define a first matchbook cover foldably connected to a second matchbook cover, said panel and the other flap being disposed between and covered by said first and second matchbook covers when the two matchbook covers are folded together, thereby to form a matchbook integral with the toothpick dispenser.

20. The toothpick dispenser of claim 19 further comprising a plurality of matches carried by said second matchbook cover between said first and second matchbook covers.

* * * * *